United States Patent [19]

Phi-Wilson et al.

[11] Patent Number: 5,232,828
[45] Date of Patent: Aug. 3, 1993

[54] COATING AGENTS FOR CELL RECOVERY

[75] Inventors: Janette T. Phi-Wilson, Belmont; Diether J. Recktenwald, Cupertino, both of Calif.

[73] Assignee: Becton, Dickinson and Company, Franklin Lakes, N.J.

[21] Appl. No.: 848,513

[22] Filed: Mar. 9, 1992

[51] Int. Cl.⁵ ............................................. A01N 1/02
[52] U.S. Cl. ...................................... 435/2; 422/102; 436/810
[58] Field of Search ............ 435/2, 261, 240.1, 240.2, 435/69.1, 172.3; 436/824, 810; 422/102

[56] References Cited

U.S. PATENT DOCUMENTS

| | | | |
|---|---|---|---|
| 3,380,584 | 4/1968 | Fulwyler | 209/3 |
| 3,710,933 | 1/1973 | Fulwyler et al. | 209/3.1 |
| 3,826,364 | 7/1974 | Bonner et al. | 209/3.1 |
| 4,148,718 | 4/1979 | Fulwyler | 209/3.1 |
| 4,175,662 | 11/1979 | Zold | 209/552 |
| 4,230,558 | 10/1980 | Fulwyler | 209/3.1 |
| 4,927,750 | 5/1990 | Dorn | 435/261 |
| 5,030,002 | 7/1991 | North, Jr. | 356/73 |

FOREIGN PATENT DOCUMENTS

| | | | |
|---|---|---|---|
| 0194212 | 9/1986 | European Pat. Off. | 435/2 |
| 0158556 | 9/1983 | Japan | 422/102 |
| 2081688 | 2/1982 | United Kingdom | 422/102 |

OTHER PUBLICATIONS

Fulwyler, Science, 150: 910–911 (1965).
IEEE Trans., Nuclear Science, NS-21, 714–720 (1973).
Duhnen et al., Histochemistry (1983) 77: 117–121.
Meck et al., Cytometry 1: 84–86 (1980).
Majuri et al., Eur. J. Haematol. 38: 21–25 (1987).
Charo, J. Biol. Chem. 262: 9935–9938 (1987).
Rennard et al., Clin. Exp. Immunol. 54: 239–247 (1983).
Grinnell, J. Cell Biol., 86: 104–112 (1980).
Patel, et al., PNAS, 82: 440–444 (1985).
Holderbaum et al., J. Cell. Physiol., 126: 216–224 (1986).

Primary Examiner—Douglas W. Robinson
Assistant Examiner—Kristin K. Larson
Attorney, Agent, or Firm—Donna R. Fugit

[57] ABSTRACT

A method for improving recovery of cells from liquid suspension by centrifuqation. The method comprises coating the interior of centrifuge containers with a solution comprising an amphipathic compound prior to introduction of the cell suspension and centrifugation. The method is suited for recovery or concentration of rare cells from dilute suspensions, for example when rare cells are isolated from a sample by sorting on a flow cytometer.

17 Claims, 2 Drawing Sheets

COATING AGENTS FOR CELL RECOVERY

FIELD OF THE INVENTION

The present invention relates to methods for recovering cells from liquid suspensions thereof and in particular to recovery, concentration or enrichment of rare cells isolated by flow cytometry.

BACKGROUND OF THE INVENTION

Flow cytometry has made it possible to analyze cells based on a variety of chemical and physical characteristics such as size, granulation of the cytoplasm and presentation of specific antigens. Flow cytometers, such as the FACScan TM instrument sold by Becton Dickinson Immunocytometry Systems (San Jose, Calif.) analyze cells on the basis of fluorescent and light scattering properties. To perform this analysis, cells are introduced into the center of a focused liquid stream which causes them to pass, one at a time, through the beam of a focused high power laser. Each cell is individually characterized by its light scatter signals and the intensity and color of fluorescence emitted in response to illumination by the laser.

In one type of cell sorting flow cytometer, after detecting the desired characteristic within an optic electronic system, the stream containing the individual cells is electrically charged shortly before being broken into droplets containing individual cells. An electrostatic field then diverts the flow of cell containing droplets into two or more streams depending on the polarity and charge of the droplets, and the divided streams are collected in separate containers. Particle sorting is described by M. J. Fulwyler in Science 150:910-911 (1965) and in IEEE Trans. on Nuclear Science, NS-21, pg. 714-720 (1973). Particle sorters which rely on electrostatic separation of particles are also described in U.S. Pat. Nos. 3,380,584; 3,710,933; 3,826,364; 4,148,718; and 4,230,558.

In another type of cell sorting flow cytometer, the particle stream is not broken into droplets for collection. Instead, the portion of the stream containing the cell of interest is collected after its detection by the optic system. This may be accomplished by deflection of the particle stream as in the fluidic switching flow sorter described by Duhnen, et. al. (Histochemistry (1983) 77:117-121) and in U.S. Pat. No. 4,175,662. Fluidic switching sorters, such as the PAS III instrument available from Partec (Muster, Germany), have a closed fluidic system and use gas controlled by piezoelectric valves to divert the fluid stream to sort cells. The closed fluidics also make this type of sorter preferable for use with infectious materials or samples which must be kept sterile.

Alternatively, the portion of the particle stream containing the desired particle may be collected by moving the catcher tube to align it with the stream at the appropriate time for collecting the particle. The catcher tube sorter does not rely on deflection of particles for sorting and therefore has the advantages of avoiding pressure pulses, minimizing damage to cells and reducing or eliminating biologically hazardous aerosols. This type of sorter is disclosed in U.S. Pat. No. 5,030,002. An example is the FACSort TM instrument (Becton Dickinson Immunocytometry Systems, San Jose, Calif.). This sorter is configured so that the catcher tube sits continuously in the edge of the fluid stream but is not aligned with the portion of the stream which contains cells until it is moved into the center of the stream to collect the desired cell. This sorter type therefore collects a relatively larger volume of fluid than does either the droplet sorter or the fluidic switching sorter, and the more rare the collected cells the more dilute the resulting cell suspension.

Cell recovery is therefore a particular problem when cells are sorted using catcher tube sorters such as the FACSort TM, as these types of particle sorters tend to produce the sorted cells in a larger volume of fluid than either fluidic switching or droplet sorters. Recovery by centrifugation is inefficient when the cell suspension is dilute, and a substantial loss of cells often results. When very few cells are present in a large volume, recovery of any cells by centrifugation may be impossible. The present invention is therefore particularly useful for recovery of cells isolated in dilute solution by flow cytometry using closed sorting systems such as the FACSort TM, but is also useful for recovering cells from dilute suspensions produced by other procedures.

Another useful application of the invention is in centrifugal cytology. In this procedure cells are sedimented out of liquid suspension onto slides for cytologic analysis. A centrifuge container, generally comprising a funnel, is used to hold the cell suspension during centrifugation and to direct the sedimented cells onto a discrete area of the slide. The Cytospin TM (Shandon) is an example of such a device. Loss of rare cells in dilute suspensions during centrifugation is also a problem in centrifugal cytology, presumably due to sticking to the walls of the funnel. Recovery of cells on slides using such procedures can be significantly improved using the methods of the invention.

Siliconizing the interior surfaces of centrifuge container is the art-recognized method for improving recovery of cells from liquid suspensions by centrifugation. Siliconization has several drawbacks, however, including the requirement for toxic chemicals such as dichlorodimethyl silane and chloroform to prepare the silicon coating. The procedure is also time consuming and cannot be used to coat polystyrene, a widely used centrifuge container material. The albumin coating methods of the invention, in contrast, are less toxic, easy to apply to a variety of materials including polystyrene, relatively inexpensive and are more effective for improving cell recovery than are silicon coatings.

Amphipathic molecules are those which contain both hydrophobic (nonpolar) regions and hydrophilic (polar regions. Proteins, fatty acids and surfactants are examples of amphipathic molecules. Of these, albumin is probably the best known in the art as a coating for a variety of surfaces and materials which come into contact with cells. R. A. Meck, et. al. (1980. Cytometry 1:84-86) describe albumin as a coating for microscope slides used to collect flow sorted cells. These authors report that fewer than half of the cells were retained on the albumin-coated slides after cytoloqical staining. R. Majuri, et. al. (1987. Eur. J. Haematol. 38:21 25) report that K562 cells do not attach to acrylic microbeads coated with albumin. Similarly, I. F. Charo, et. al. (1987. J. Biol. Chem. 262:9935-9938) teach that HUVE cells failed to adhere to albumin-coated glass slides. S. I. Rennard, et. al. (1983. Clin. Exp. Immunol. 54:239-247) disclose that no attachment of CHO cells occurred on albumin coated plastic petri dishes. F. Grinnell (1980. J. Cell Biol. 86:104-112) reported that latex beads coated with bovine albumin did not support binding of baby hamster kidney cells. V. P. Patel, et. al. (1985. PNAS 82:440 444) disclose that reticulocytes do not attach to albumin-coated plastic petri dishes. In contrast, D. Holderbaum, et. al. (1986. J. Cell. Physiol. 126:216-224) report attachment and growth of rabbit arterial smooth muscle cells to plastic culture dishes coated with bovine serum albumin. Therefore, although albumin is known in the art as a coating for a variety of surfaces and materials which come into contact with cells, such coatings were not previously known as a means to improve recovery of cells from liquid suspensions by centrifugation.

Block polymer surfactants, such as the Pluronic® and Tetronic® polyols (BASF Wyandotte Corp., Parsippany, NJ) are amphipathic molecules which comprise ethylene oxide and propylene oxide groups added to a base molecule (propylene glycol for Pluronic® and ethylenediamine for Tetronic®). The hydrophilic regions containing polyethylene oxide and the hydrophobic regions containing polypropylene oxide provide the surfactant properties. These surfactants and others like them are known in the art for foam control, emulsification, wetting, etc. They were not previously known as agents for improving recovery of cells from liquid suspension by centrifugation. Further, the utility of amphipathic molecules in general for this purpose has not previously been recognized.

SUMMARY OF THE INVENTION

It has been discovered that recovery and/or concentration of cells from liquid suspensions by centrifugation can be improved by coating the centrifugation container with a solution comprising an amphipathic compound prior to placing the cell suspension into the container. Amphipathic compounds suitable for use in the invention include but are not limited to nonionic surfactants such as Tetronic® and Pluronic® or proteins such as albumins. A 0.1%-5.0% solution of the amphipathic compound is preferred for coating the container. The method is particularly useful for recovering rare cells which may be contained in a relatively large volume of liquid after sorting by flow cytometry and for recovery of rare cells by centrifugal cytology. Using the coated centrifugation containers of the present invention, over 95% of cells may be recovered from the suspension by centrifugation without significant damage to the cells or loss of viability.

The present invention provides an improved method for recovering and/or concentrating cells by centrifugation, particularly recovering and/or concentrating rare cells present in dilute liquid suspension.

The present invention further provides an improved method for recovering and/or concentrating cells isolated and sorted by flow cytometry, particularly rare cells present in dilute liquid suspensions after sorting.

DETAILED DESCRIPTION OF THE INVENTION

Figure 1:
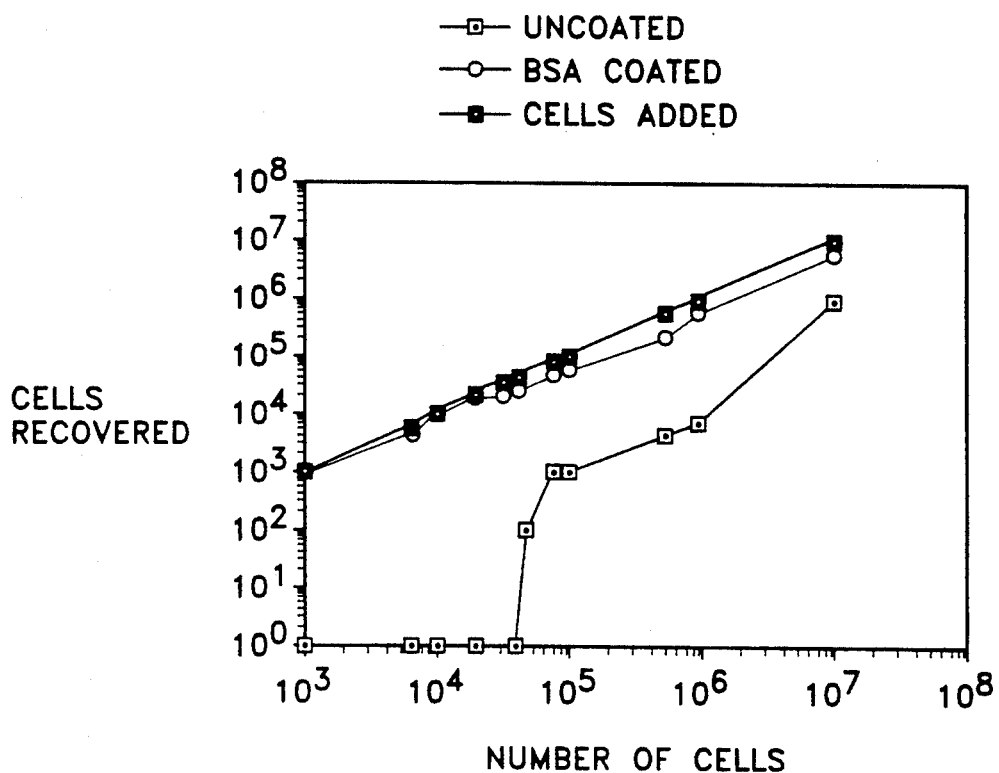
FIG. 1 is a graph of the data obtained in Example 1, comparing cell recovery from bovine serum albumin (BSA) coated polystyrene tubes with cell recovery from uncoated polystyrene tubes and with the number of cells placed in the tube prior to centrifugation.

Cells in liquid suspension are customarily recovered and/or concentrated by centrifugation. It has now been discovered that recovery of cells in liquid suspension is significantly improved when centrifuge containers having an interior coating of a solution comprising an amphipathic compound are used for centrifugation of the cell suspension. Cell recovery is especially improved for dilute suspensions of cells, making the invention particularly useful for recovery of rare cells sorted by flow cytometry and for depositing cells onto slides by centrifugal cytology. In addition, use of amphipathic compound coated containers during centrifugation improves the viability of recovered cells.

In the practice of the invention, prior to placing a cell suspension in a centrifuge container, a 0.1%-5% solution of an amphipathic compound is used to coat the interior of the container. In general, the solution is sterilized, preferably by filter sterilization. Suitable amphipathic compounds for use in the invention include, but are not limited to, albumin (e.g., human serum albumin or bovine serum albumin) and surfactants (e.q., Pluronics® and Tetronics® available from BASF Wyandotte Corp., Parsippany, NJ). Preferably the coating solution comprises about 2-5% bovine serum albumin (BSA), most preferably about 4-5% BSA. Optionally, a preservative such as sodium azide may be included in the coating solution at about 0.02-0.2% to inhibit microbial growth. About 0.2% sodium azide is preferred, as the higher concentration compensates for dilution of the coating by addition of the cell suspension to the coated container.

The container to be coated may be glass, plastic, polystyrene or polypropylene and is preferably a tube or bottle suitable for use in a centrifuge or a device for depositing cells on a slide by centrifuqation.

To coat the centrifuge container, a solution of an amphipathic compound as described above is placed therein in an amount sufficient to fill the container to the desired level of coating. The container is then incubated for about 10 minutes to 2 days. Preferably, the incubation step is performed at about 4° C. (e.g., on ice or in a refrigerator) for about 1-3 hours. Following the incubation step, the container is emptied of coating solution by removing excess liquid, leaving a coating comprising the amphipathic compound o the interior of the container. The cell suspension may be placed in the coated container while the coating is still wet or the coating may be dried prior to adding the cell suspension. If the coating is dried, it is preferably freeze-dried or air dried. Freeze drying is most preferred of the dried coating methods. In a most preferred embodiment, the cell suspension is added to the coated container without drying the coating and the cell suspension is in a physiological buffer such as phosphate buffered saline.

Preferably, the centrifuge containers are plastic, polystyrene or polypropylene tubes or bottles, or centrifugal cytology devices coated for about 1-3 hours at about 4° C. with a solution of about 4% BSA/0.2% sodium azide in a suitable buffer. Preferably the coated containers are used for recovery and/or concentration of cells without drying of the BSA coating.

To use the coated containers for recovery or concentration of cells, a cell suspension from which the cells are to be recovered or concentrated is placed in the coated container and centrifuged to sediment the cells. Preferably, the cells are sorted into coated collection tubes or centrifugal cytology devices using flow cytometry and subsequently centrifuged in the collection tubes or devices to sediment the cells. Generally, centrifugation at about 300 xq for about 10-15 min. is sufficient to sediment the cells without significant damage or loss of viability. However, it is within the ordinary skill in the art to adjust the parameters of centrifugation to optimize cell recovery and viability for a particular application. Following sedimentation by centrifugation, the supernatant is generally removed from the container or the slide is removed from the centrifugal cytology device prior to further processing of the recovered cells.

The compositions and methods set forth herein represent certain embodiments of the principles of the invention. It is to be understood that the present invention may be embodied in numerous alternative fashions and that such alternative embodiments may be conceived by those skilled in the art using only routine abilities and without departing from the spirit and scope of the invention. Specific illustrative embodiments are set forth in the following. Examples but are not to be considered as limiting the scope of the invention as defined by the appended claims and their equivalents.

RECOVERY FROM DILUTE SUSPENSION IN BSA COATED AND UNCOATED TUBES

The effect of bovine serum albumin (BSA) coating on cell recovery at various concentrations of cells was tested in polystyrene tubes coated with 4% BSA in phosphate buffered saline (PBS—1.022 g/L sodium phosphate, 8.766 q/L sodium chloride, 0.381 g/L potassium phosphate, pH 7.0-7.3) for 1 hr. on ice. Varying numbers of peripheral blood mononuclear cells (PBMC) in 15 ml of PBS were added to coated and uncoated tubes, centrifuged at about 300 xg for about 10 min. and the number of recovered cells counted in a hemacytometer. The results are shown in the following table and depicted graphically in FIG. 1:

| # Cells/Tube | # Cells Recovered | |
| --- | --- | --- |
| | BSA Coated | Uncoated |
| 1000 | 1000 | 0 |
| 5000 | 4000 | 0 |
| 10,000 | 9000 | 0 |
| 20,000 | 18,000 | 0 |
| 40,000 | 22,000 | 0 |
| 50,000 | 28,000 | 100 |
| 80,000 | 46,000 | 1000 |
| 100,000 | 65,000 | 1,000 |
| 500,000 | 250,000 | 5,000 |
| 1,000,000 | 615,000 | 7,000 |
| 10,000,000 | 5,400,000 | 1,070,000 |

The BSA coated tubes allowed a high percentage of cell recovery even at very dilute concentrations of cells. Surprisingly, the % recovery increased with decreasing concentration of cells when BSA coated tubes were used. In contrast, no cells could be recovered from uncoated tubes at low concentrations of cells.

EXAMPLE 2

RECOVERY OF CELLS FROM DILUTE SUSPENSION IN NONIONIC SURFACTANT COATED TUBES

PBMC s were prepared as in Example 1 and adjusted to a concentration of approximately $1 \times 10^6$ cells/ml in PBS. Two 15 ml polystyrene tubes for each coating were filled with filter sterilized (1) 4% BSA in PBS, 0.2% $NaN_3$, 2) 0.4% Pluronics F68 in PBS, 0.2% $NaN_3$, and 3) 0.2% Tetronics 701 in PBS, 0.2% $NaN_3$. Two control tubes filled with PBS were also prepared. The tubes were incubated for 1.5 hrs. on ice. After incubation, the solutions were removed and replaced with 14 ml of PBS and 50 μL of cell suspension (about 55,000 cells). Tubes were inverted three times each to mix and centrifuged for 10 min. at $300 \times g$. The supernatant was removed, leaving about 50 μL of residual PBS. Acridine orange and ethidium bromide (50 μL) were added and mixed. The recovered cells were counted in a hemacytometer to determine the number of cells recovered and % recovery.

In the uncoated control tubes, an average of 0.5% of cells were recovered. In contrast, cell recovery from the BSA coated tubes averaged 81.5%. The nonionic surfactant coated tubes also significantly improved cell recovery as compared to controls, although not to the same extent as BSA, averaging 57.5% from Pluronics F68 coated tubes and 47.5% from Tetronics 701 coated tubes.

EXAMPLE 3

OPTIMIZATION OF COATING PROCEDURES

Tubes and cells were prepared as in Example 1, using 30,000 cells per tube and a 5% BSA coating solution. Cell viability prior to centrifugation was about 94%. After various incubation times at 4° C., the BSA solution was poured off. One set of tubes was used with the coating still wet and a duplicate set of tubes was allowed to dry before adding the cell suspension.

With a 1 or 2 hr. coating period, more than 90% of the cells were recovered with only a 2% loss of viability (i.e., 8% inviable cells). Recovery and viability results were the same for both the dry and the wet coatings when incubation was for 1 or 2 hr. In tubes coated for 10 min., 40% of the cells were recovered with 30% inviable cells when the BSA coating was allowed to dry prior to use. Using the wet BSA coating with a 10 min. incubation, 24% of the cells were recovered with 17% inviable cells. In uncoated tubes, only 8% of the cells were recovered and all appeared to be inviable. It was observed that although improved recovery of cells was obtained using the dried BSA coating, in tubes where the BSA was kept wet prior to addition of PBS the cells appeared more distinct and there was less debris.

These results show a significant improvement in cell recovery from dilute suspensions when the albumin coating is used. The improvement was seen regardless of whether the coating was wet or allowed to dry prior to addition of the cell suspension. Coating for 1 to 2 hours gave significantly improved results compared to both controls and tubes coated for 10 min. However, even with a 10 min. coating time cell recovery was markedly improved compared to control uncoated tubes.

Figure 2:
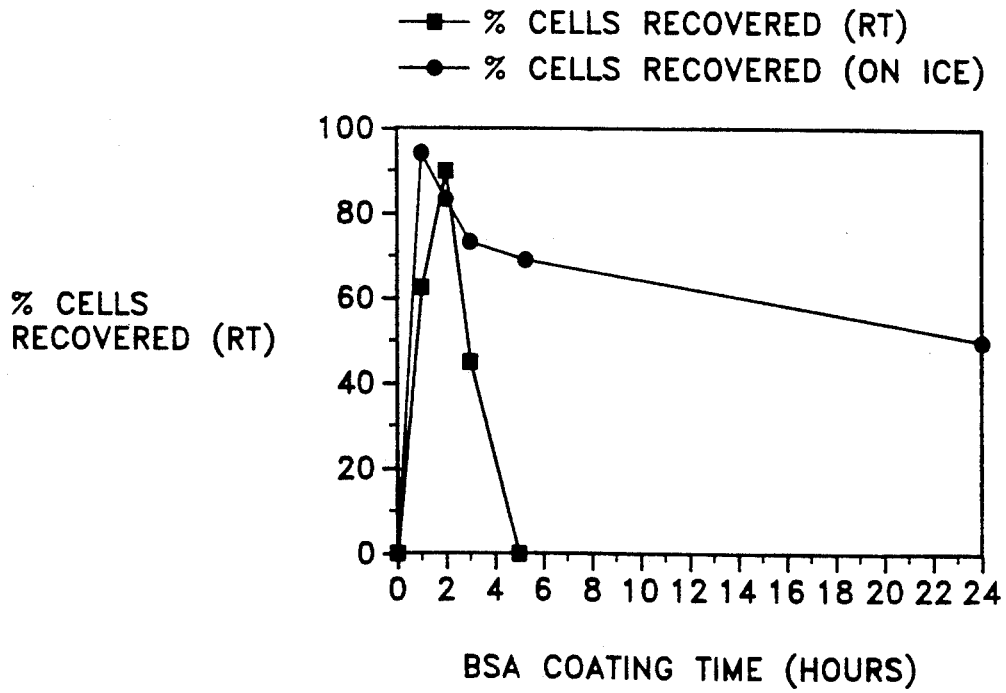
FIG. 2 is a graph of the data obtained in Example 3, comparing cell recovery from BSA coated tubes at varying coating times and temperatures.

Optimization experiments were also performed under conditions of cell recovery after sorting. Collection tubes for use with the FACSort™ cell sorting system were coated for varying periods of time at room temperature or on ice with a solution comprising 4% BSA/0.2% sodium azide. Peripheral Blood Leukocytes (PBL's) were sorted, collecting 10,000 cells in each tube. The volume of liquid collected was approximately 7.5 ml in each tube. After collection, the tubes were centrifuged to sediment the cells and recovery was calculated as previously described. The number of cells recovered of the 10,000 collected in each tube is shown in FIG. 2.

As can been seen in the graph, the results show that the incubation time and temperature for coating the tubes is critical for improving cell recovery by centrifugation. When coating at room temperature cell recovery was most improved with coating times of about 1–3 hours. After 3 hr. cell recovery was no longer enhanced. When coating on ice, the optimum cell recovery was also obtained with coating times of 1–3 hours. After 3 hrs. enhancement of cell recovery decreased slightly and gradually up to 24 hrs. but was not eliminated as it was with longer incubation times at room temperature. However, both at room temperature and on ice, the shortest and longest coating times tested resulted in reduced cell recovery as compared to coating for about 1–3 hours.

EXAMPLE 4

OPTIMIZATION OF BSA CONCENTRATION

BSA solutions of varying concentrations were made in PBS and filter sterilized using a 0.22 micron filter. Tubes were coated with the BSA solutions as in Example 1. In two sets of five tubes each (Set #1 and Set #2 below) the BS solutions were drained off after coating and replaced with an equal volume of PBS containing 5,000 PBMC. In a third set of tubes (Set #3 below) the BSA solutions were drained off after coating and replaced with an equal volume of filter sterilized 5% fetal calf serum (FCS) in PBS and 5,000 cells. As controls, two uncoated tubes were filled with 5% FCS in PBS and 5,000 cells.

The cells were centrifuged at 300 xq for 10 min. The recovered cells, contained in a residual volume of about 20 μL, were counted in a hemacytometer. The number of cells recovered from each tube is shown in the following table:

| | BSA Concentration | | | | |
|---|---|---|---|---|---|
| Treatment | 0.1% | 0.5% | 1.0% | 2.0% | 4.0% |
| Set #1 | 400 | 3600 | 4000 | 4200 | 4600 |
| Set #2 | 1200 | 1200 | 1800 | 1800 | 4400 |
| Set #3 | 1500 | 1800 | 2100 | 1900 | 1400 |

In the two uncoated control tubes, 1,000 and 1,400 of the starting 5,000 cells were recovered, respectively.

Examples 3 and 4 demonstrate that the coating conditions and albumin content of the coating are critical for obtaining efficient recovery of cells by centrifuqation according to the invention. The number of cells recovered was most improved as compared to uncoated tubes when the coating solution contained at least about 1.0% BSA and when the tubes were coated for about 1–3 hours. When coated on ice, the improvement was extended up to at least 24 hrs. In contrast, when the coating was 0.1% BSA it had essentially no effect on cell recovery as compared to controls. The best recovery was obtained using 4–5% BSA and coating for 1–3 hrs. either at room temperature or on ice. FCS, when included in the cell suspension medium, interfered with cell recovery from BSA coated tubes. While not wishing to be bound by any particular mechanism of action, Applicants believe that FCS makes the surface of the cells more sticky negating the effects of the albumin coating.

The molecules of the amphipathic coating materials of the invention have both hydrophobic and hydrophilic regions. The hydrophobic properties of many of the materials used in making centrifuge containers may attract cells, causing them to stick to the container and preventing sedimentation by centrifugation. While not wishing to be bound by any particular theory of the mechanism by which the invention works, Applicants believe the foregoing results are consistent with an interpretation in which the hydrophobic region(s) of the amphipathic compound attaches to the surface of the container. The hydrophilic regions of the molecules then orient toward the aqueous medium. The hydrophilic regions therefore mask the hydrophobic regions of the compound and the container surface, preventing loss of cells by binding. These results are also believed to be consistent with the observed criticality of coating time, as longer coating times may result in increased disorientation of the coating molecules as the coating becomes thicker, resulting in reduced effectiveness.

EXAMPLE 5

COMPARISON OF BSA COATED AND SILICONIZED TUBES

To test recovery of cells from BSA coated polystyrene tubes as compared to siliconized polypropylene tubes, seven polystyrene tubes were coated for 1 hour on ice with a solution comprising 4% BSA. A second series of seven siliconized polypropylene tubes was prepared using Surfasil™ (Pierce). Briefly, taking all necessary safety precautions, a 2% Surfasil™ solution in chloroform was prepared and the tubes were immersed in it for 5 min. The coated tubes were rinsed in tap water, air dried and baked at 65° C..

Figure 3:
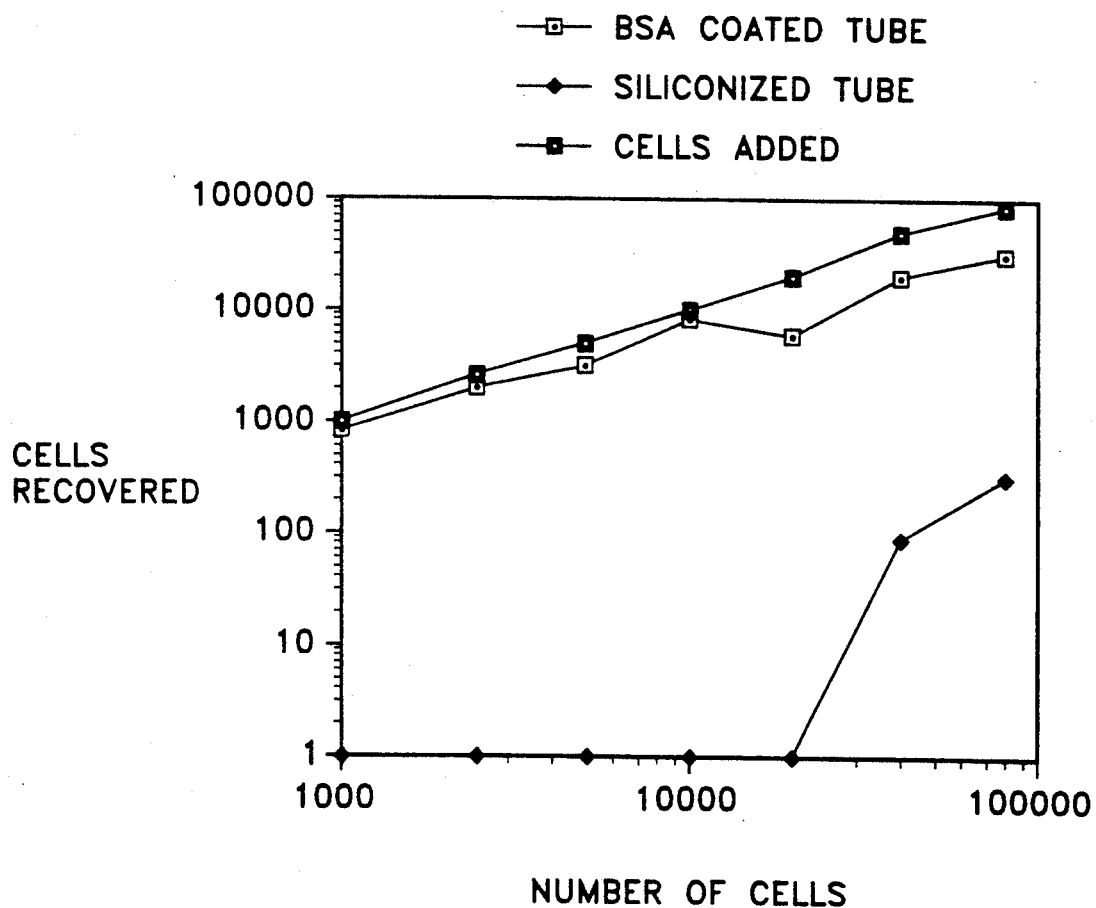
FIG. 3 is a graph of the data obtained in Example 5, comparing cell recovery from BSA coated polystyrene tubes with cell recovery from siliconized polypropylene tubes and with the number of cells placed in the tube prior to centrifugation.

To the first tube of each series was added 160,000 cells in 15 ml of PBS. The cell suspension was then serially diluted into the remaining tubes of the set. After centrifuging at 350 xq for 10 min. the residual volume was determined and the recovered cells were counted for calculation of % recovery. The results are shown in the following table and are depicted graphically in FIG. 3:

| | # Cells Recovered | | % Recovery | |
|---|---|---|---|---|
| # Cells/Tube | BSA | Silicon | BSA | Silicon |
| 80,000 | 37,200 | 300 | 47% | 0.4% |
| 40,000 | 25,500 | 100 | 64% | 0.2% |
| 20,000 | 5,950 | 0 | 30% | 0 |
| 10,000 | 7,800 | 0 | 78% | 0 |
| 5,000 | 3,000 | 0 | 60% | 0 |
| 2,500 | 2,100 | 0 | 84% | 0 |
| 1,000 | 900 | 0 | 90% | 0 |

Cell recovery from BSA coated tubes was significantly higher than recovery from siliconized tubes. The advantage of the BSA coated tubes is most apparent at lower concentrations of cells, where the % recovery surprisingly showed a trend toward increasing cell recovery as the cell suspension became more dilute. In contrast, as would be expected, using siliconized tubes the % recovery decreased a the cell suspension became more dilute.

EXAMPLE 6

RECOVERY OF CELLS AFTER FLOW SORTING

Using the FACSort ™ system, 20,000 viable PBL's were sorted into each of three polystyrene tubes coated with a solution comprising 5% BSA and three uncoated polystyrene tubes. After centrifuging to sediment the cells as previously described, cell recovery was calculated as before. Using the BSA coated collection tubes, 65% 100% of the sorted cells were recovered. In contrast, no more than 5% of collected cells were recovered from uncoated tubes.

Recovery of cells from dilute suspensions was again found to be most improved for the more dilute cell suspensions. Using the FACSort ™, varying numbers of PBL's were sorted into 15 ml. polypropylene tubes coated with a solution comprising 5% BSA. Calculation of cell recovery after centrifuqation was as follows:

| # Collected | # Recovered | |
|---|---|---|
| | Coated Tube | Uncoated Tube |
| 1,000 | 1,000 | 0 |
| 5,000 | 4,000 | 0 |
| 10,000 | 9,000 | 0 |
| 20,000 | 18,000 | 0 |
| 40,000 | 22,000 | 0 |
| 80,000 | 46,000 | 0 |
| 100,000 | 39,000 | 1,000 |

What is claimed is:

1. A method for increasing recovery of cells from a liquid suspension by centrifugation comprising the steps of placing cell suspension into a container having an interior coating comprising an albumin, centrifuging the container such that the cells are sedimented and recovering the sedimented cells.

2. The method according to claim 1 wherein the cell suspension is placed into a container having an interior coating comprising an albumin.

3. The method according to claim 2 wherein the cell suspension is placed into a container having an interior coating comprising bovine serum albumin.

4. The method according to claim 3 wherein the coating is applied to the interior of the container by contacting the interior of the container with a solution comprising about 1.0-5% bovine serum albumin.

5. The method according to claim 4 wherein the coating is applied to the interior of the container by contacting the interior of the container with a solution comprising about 2-5% bovine serum albumin.

6. The method according to and one of claims 1, 2, 3, 4 or 5 wherein the interior coating is dried prior to placing the cell suspension in the container.

7. The method according to any one of claims 1, 2, 3, 4 or 5 wherein the interior coating is wet prior to placing the cell suspension therein.

8. The method according to any one of claims 1, 2, 3, 4, or 5, wherein the cell suspension is placed into a container having an interior coating which further comprises a preservative.

9. The method according to claim 8 wherein the coating is applied to the interior of the container by contacting the interior of the container with a solution further comprising 0.02-0.2% azide.

10. The method according to claims 4 or 5 wherein the interior of the container is contacted with the solution for about 1-3 hr.

11. A method for increasing recovery of cells from a liquid suspension by centrifugation comprising the steps of placing the cell suspension into a container having an interior coating comprising bovine serum albumin, centrifuging the container such that the cells are sedimented and recovering the cells, the coating being applied to the container by contacting the interior thereof with a solution comprising about 4% bovine serum albumin.

12. The method according to claim 11 wherein the coating is applied by contacting the interior of the container with the solution for about 1-3 hr. at about 4° C.

13. A method of increasing recovery of cells from a liquid suspension thereof comprising the steps of:
  (a) sorting the cells by flow cytometry into a container having an interior coating comprising an albumin;
  (b) centrifuging the container such that the cells are sedimented, and;
  (c) recovering the sedimented cells.

14. The method according to claim 13 wherein the cells are sorted into a container having an interior coating comprising bovine serum albumin.

15. The method according to claim 14 wherein the coating is applied to the interior of the container by contacting the interior of the container with a solution comprising about 1-5% bovine serum albumin.

16. The method according to claim 15 wherein the cells are sorted into a container having an interior coating further comprising a preservative.

17. The method according to claim 16 wherein the coating is applied to the interior of the container by contacting the interior of the container with a solution further comprising about 0.02-0.2% sodium azide.

* * * * *